(12) United States Patent
Sathe et al.

(10) Patent No.: US 11,331,283 B2
(45) Date of Patent: May 17, 2022

(54) PHARMACEUTICAL COMPOSITIONS COMPRISING CINACALCET HYDROCHLORIDE AND ONE OR MORE BINDERS

(71) Applicant: UNICHEM LABORATORIES LTD, Mumbai (IN)

(72) Inventors: Dhananjay Sathe, Thane (IN); Srikant Pimple, Pune (IN); Pravin Kumar Maurya, Pune (IN)

(73) Assignee: UNICHEM LABORATORIES LTD, Mumbai (IN)

( * ) Notice: Subject to any disclaimer, the term of this patent is extended or adjusted under 35 U.S.C. 154(b) by 5 days.

(21) Appl. No.: 16/637,922

(22) PCT Filed: Aug. 13, 2018

(86) PCT No.: PCT/IB2018/056084
§ 371 (c)(1),
(2) Date: Feb. 10, 2020

(87) PCT Pub. No.: WO2019/034981
PCT Pub. Date: Feb. 21, 2019

(65) Prior Publication Data
US 2020/0215002 A1   Jul. 9, 2020

(30) Foreign Application Priority Data
Aug. 16, 2017 (IN) .............................. 201721028980

(51) Int. Cl.
*A61K 31/135* (2006.01)
*A61K 9/20* (2006.01)

(52) U.S. Cl.
CPC .......... *A61K 31/135* (2013.01); *A61K 9/2095* (2013.01)

(58) Field of Classification Search
CPC .. A61K 31/135; A61K 9/2095; A61K 9/1652; A61K 9/2054; A61K 31/137; A61P 5/18
See application file for complete search history.

(56) References Cited

U.S. PATENT DOCUMENTS

| | | | | |
|---|---|---|---|---|
| 7,829,595 B2 * | 11/2010 | Lawrence | .............. | A61K 31/00 514/579 |
| 2011/0287065 A1 * | 11/2011 | Neville | ................ | A61K 9/5146 424/400 |
| 2011/0295037 A1 * | 12/2011 | Szekeres | ................ | C07C 209/84 564/387 |
| 2015/0328172 A1 * | 11/2015 | Murpani | .............. | A61K 9/2027 424/465 |

FOREIGN PATENT DOCUMENTS

CN       102885792 A     1/2013

OTHER PUBLICATIONS

International Search Report dated Dec. 13, 2018 in PCT/IB2018/056084 filed on Aug. 13, 2018.

* cited by examiner

*Primary Examiner* — Snigdha Maewall
(74) *Attorney, Agent, or Firm* — Oblon, McClelland, Maier & Neustadt, L.L.P.

(57) ABSTRACT

A pharmaceutical composition containing cinacalcet or pharmaceutically acceptable salts thereof and one or more pharmaceutically acceptable excipients. A pharmaceutical composition containing cinacalcet or pharmaceutically acceptable salts thereof having a particle size distribution $D_{90}$ equal to or less than 20 μm, $D_{50}$ equal to or less than 10 μm, and $D_{10}$ equal to or less than 5 μm and one or more and binders in an amount of 0.9% w/w or less, relative to the total weight of composition, where the composition is not free of binder and that the total amount of binder does not exceed 0.9% w/w relative to the total weight of the composition.

12 Claims, 5 Drawing Sheets

Continued

PHARMACEUTICAL COMPOSITIONS COMPRISING CINACALCET HYDROCHLORIDE AND ONE OR MORE BINDERS

FIELD OF THE INVENTION

The present invention relates to a pharmaceutical composition comprising cinacalcet or pharmaceutically acceptable salts thereof and one or more pharmaceutically acceptable excipients. Particularly the present invention relates to a pharmaceutical composition comprising cinacalcet or pharmaceutically acceptable salts thereof and one or more binders in an amount 0.9% w/w or less, relative to the total weight of composition. The present invention also relates to process for preparation of composition comprising cinacalcet or pharmaceutically acceptable salts thereof.

BACKGROUND OF THE INVENTION

Cinacalcet is calcimimetic drug which acts by allosteric activation of the calcium-sensing receptor and it is indicated for the treatment of secondary hyperparathyroidism and for the treatment of hypercalcemia in patients with parathyroid carcinoma.

The IUPAC name for cinacalcet is, (R)—N-[1-(1-naphthyl)ethyl]-3-[3-(trifluoromethyl)phenyl]propan-1-amine, is described in U.S. Pat. No. 6,211,244. The hydrochloride salt of cinacalcet is described chemically as N-[1-(R)-(–)-(1-naphthyl)ethyl]-3-[3(trifluoromethyl)phenyl]-1-aminopropane hydrochloride and has the following structural formula:

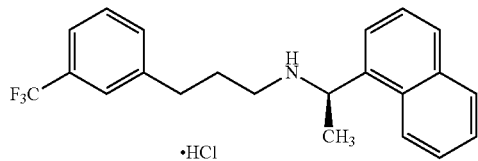 [SMILES: C[C@@H](NCCCc1cccc(C(F)(F)F)c1)c1cccc2ccccc12 ; Cl]

Cinacalcet hydrochloride is currently available in the market as tablet for oral use under the brand name Sensipar® in USA and Mimpara® inEurope market.

U.S. Pat. Nos. 7,829,595 and 9,375,405 by Amgen, disclose cinacalcet composition containing a binder in an amount from about 1% to about 5% of total weight of composition. Inventive step and novelty of U.S. Pat. Nos. 7,829,595 and 9,375,405 is limited only to the attributes claimed i.e. 1-5% w/w of binder. Presence of colloidal silicon dioxide is an important and critical attribute of the composition claimed by U.S. Pat. No. 7,829,595.

IN2250/CHE/2014 patent application by Appcure Labs, discloses a pharmaceutical composition comprising cinacalcet and its pharmaceutically acceptable salts and one or more pharmaceutically acceptable excipients, wherein the composition is free of binder. Though it discloses the composition to be free of binder, it does disclose the composition comprising a binder in the range from 5%-10% by weight relative to the total weight of the composition. Moreover, the invention discloses that the term "free" means less than 1% w/w by weight, specifically less than 0.5% w/w by weight and more specifically 0% w/w by weight of binder, however, the specification is devoid of the experimental data, reproducibility and working of such a composition, excluding composition containing 0% w/w by weight of the binder. Thus, there is no teaching for the preparation of cinacalcet composition that contains binder at a lower concentration, especially less than 1% w/w of the composition. Furthermore product profile is always vulnerable to several factors and binder concentration is one of the most critical factor that determines attributes of dissolution and hence subsequent bioavailability. Thus the specification is inadequate and does not to enable or support the claims having binder from 0.1% to 1% w/w of composition. Further, the composition comprising combination of binders is not disclosed in this invention. The specification is silent on dissolution profile, stability, shelf life and the bioequivalence of the product of invention. Specification is inadequate as it does not describe similarity factor in comparison with the innovator composition. Further there is ambiguity if the compositions described by this application are bioequivalent. The composition that exhibits f2 more than 50% would not necessarily be bioequivalent. Therefore this invention is more relevant for the composition which is free of binder or which comprises much higher amount of 5-10% w/w by weight of binder relative to the total weight of the composition.

US20150306049 patent application by K.H.S. Pharma Holding GMBH, discloses a pharmaceutical composition of cinacalcet, wherein the composition comprises from 15 to 50% by weight cinacalcethydrochloride, from 30 to 80% by weight of one or more fillers and from 5.1% to 7% by weight of one or more binders. The specific formulation contains high percentage of binder that is more than 5% w/w to the total weight of total composition.

US20150328172 patent application by Synthon BV, discloses a pharmaceutical composition of cinacalcet, wherein the composition comprises a therapeutically effective dose of cinacalcet hydrochloride in an amount from 45% to 55% by weight;
from 30% to 50% of pregelatinized starch by weight based on the total weight of the composition; at least one binder in an amount of from 1% to 5% by weight based on the total weight of the composition; a disintegrant in an amount of from 1% to 10% by weight based on the total weight of the composition; a lubricant and a glidant in a total amount of from 0.05% to 5% by weight based on the total weight of the composition, and wherein the cinacalcet hydrochloride has a $D_{90}$ equal to or less than 30 μm.

US2016143863 patent application by Jubilant Life Sciences Ltd., discloses an immediate release pharmaceutical composition, comprising from about 10 to 60% by weight cinacalcet or its pharmaceutically acceptable salts; from about 20.0 to 80.0% by weight of one or more diluents; and from about 1.0% to 8.0% by weight of one or more binders; wherein the immediate release pharmaceutical composition is substantially free of disintegrating agent.

IN35/CHE/2014 patent application by Hetero Labs Limited, discloses a binder free immediate release tablet composition comprising cinacalcet and one or more pharmaceutically acceptable excipients. This patent application also discloses that the invention is free of particular binders listed in the embodiment of IN35/CHE/2014 which are present in the range from 1% to 10% of the total composition. The patent application does not disclose any illustrative example of composition containing less than 1% binder.

WO2015136329PCT application by Abdi Ibrahim Ilac discloses a binder free pharmaceutical composition comprising cinacalcet or pharmaceutically acceptable salt thereof and at least one or more excipients, the composition is prepared by wet granulation. The application discloses that the composition is free of binding agent; specifically the composition does not contain polyvinylpyrrolidone or copovidone.

Binder free compositions produce weak bonding during granulation and it affects the dissolution profile and hence bioavailability of the product. Also use of more than 5% binder in the composition results in the risk of over-granulation and of tablet hardening during storage over a longer time. Moreover the presence of binder in a formulation in higher quantity also requires the addition of (strong) disintegrants for rapid dissolution.

Hence there is unmet need to provide a more stable, reproducible, cost effective and bioequivalent composition comprising cinacalcethydrochloride.

OBJECT OF THE INVENTION

The main object of the present invention to provides a pharmaceutical composition comprising cinacalcet or pharmaceutically acceptable salts thereof and one or more binders in an amount of 0.9% w/w or less relative to the total weight of composition, wherein the composition is not free of binder and that the total amount of binder does not exceed 0.9% w/w relative to the total weight of the composition.

Yet another main object of the present invention to provide a pharmaceutical composition comprising cinacalcet or pharmaceutically acceptable salts thereof and one or more binders in an amount of 0.9% w/w or less, preferably about 0.7% w/w or less, more preferably about 0.4% w/w or less, relative to the total weight of the composition.

Yet another object of the present invention is to provide a pharmaceutical composition comprising cinacalcet or pharmaceutically acceptable salts thereof and povidone in an amount of 0.9% w/w or less, preferably about 0.7% w/w or less, more preferably about 0.4% w/w or less, relative to the total weight of the composition.

Yet another object of the present invention is to provide a pharmaceutical composition comprising cinacalcet or pharmaceutically acceptable salts thereof and multiple binders such that the total weight of the binder or concentration of binder is less than 0.9% w/w or less, preferably about 0.7% w/w or less relative to the total weight of the composition.

Yet another object of the present invention is to provide a pharmaceutical composition comprising cinacalcet or pharmaceutically acceptable salts thereof and povidone in an amount of 0.9% w/w or less, preferably about 0.7% w/w or less, more preferably about 0.4% w/w or less, relative to the total weight of the composition and pregelatinized starch in an amount of 0.9% w/w or less, preferably about 0.7% w/w or less, more preferably about 0.4% w/w or less, relative to the total weight of the composition such that the total amount of binder does not exceed 0.9% w/w relative to the total weight of the composition.

Yet another object of the present invention is to provide a pharmaceutical composition comprising cinacalcet or pharmaceutically acceptable salts thereof and preferably povidone present in an amount of about 0.4% w/w or less and pregelatinized starch present in an amount of about 0.4% w/w or less, still more preferably povidone present in an amount of about 0.35% w/w and pregelatinized starch present in an amount of about 0.35% w/w relative to the total weight of the composition.

Yet another object of the present invention is to provide a process for preparing pharmaceutical composition comprising cinacalcet or pharmaceutically acceptable salts thereof and one or more binders. The process can be selected from wet granulation, dry granulation, direct compression and compaction method.

SUMMARY OF THE INVENTION

In an aspect, the present invention relates to a pharmaceutical composition comprising cinacalcet or pharmaceutically acceptable salts thereof and one or more pharmaceutically acceptable excipient.

In one aspect, the present invention provides a pharmaceutical composition comprising cinacalcet or pharmaceutically acceptable salts thereof and one or more binders in an amount of 0.9% w/w or less relative to the total weight of composition, wherein the composition is not free of binder and that the total amount of binder does not exceed 0.9% w/w relative to the total weight of the composition.

In another aspect, the present invention provides a pharmaceutical composition comprising cinacalcet or pharmaceutically acceptable salts thereof and povidone in an amount of 0.9% w/w or less, preferably about 0.7% w/w or less, more preferably about 0.4% w/w or less, relative to the total weight of the composition.

In yet another aspect, the present invention provides a pharmaceutical composition comprising cinacalcet or pharmaceutically acceptable salts thereof and povidone in an amount of 0.9% w/w or less, preferably about 0.7% w/w or less, more preferably about 0.4% w/w or less, relative to the total weight of the composition and pregelatinized starch in an amount of 0.9% w/w or less, preferably about 0.7% w/w or less, more preferably about 0.4% w/w or less, relative to the total weight of the composition such that the total amount of binder does not exceed 0.9% w/w relative to the total weight of the composition.

In another aspect, the present invention provides the pharmaceutical composition of cinacalcet, wherein the composition comprises cinacalcet hydrochloride.

Another aspect of the present invention provides a process for preparation of the pharmaceutical composition comprising cinacalcet or pharmaceutically acceptable salts thereof and at least one pharmaceutically acceptable excipient.

In yet another aspect, the present invention provides a process for preparing pharmaceutical composition of the present invention, the process comprising:
a) mixing cinacalcet or pharmaceutically acceptable salts thereof with one or more pharmaceutically acceptable excipients;
b) granulating the mixture obtained in step a);
c) drying the granules obtained in step b) followed by blending, lubrication and compression; and
d) optionally coating the dosage form obtained in step c).

BRIEF DESCRIPTION OF THE DRAWING

Features and advantages of the subject matter of the present invention as disclosed herein will become clearer from the detailed description of an embodiment thereof, with reference to the attached drawing, given purely by way of an example, in which.

Figure 1:
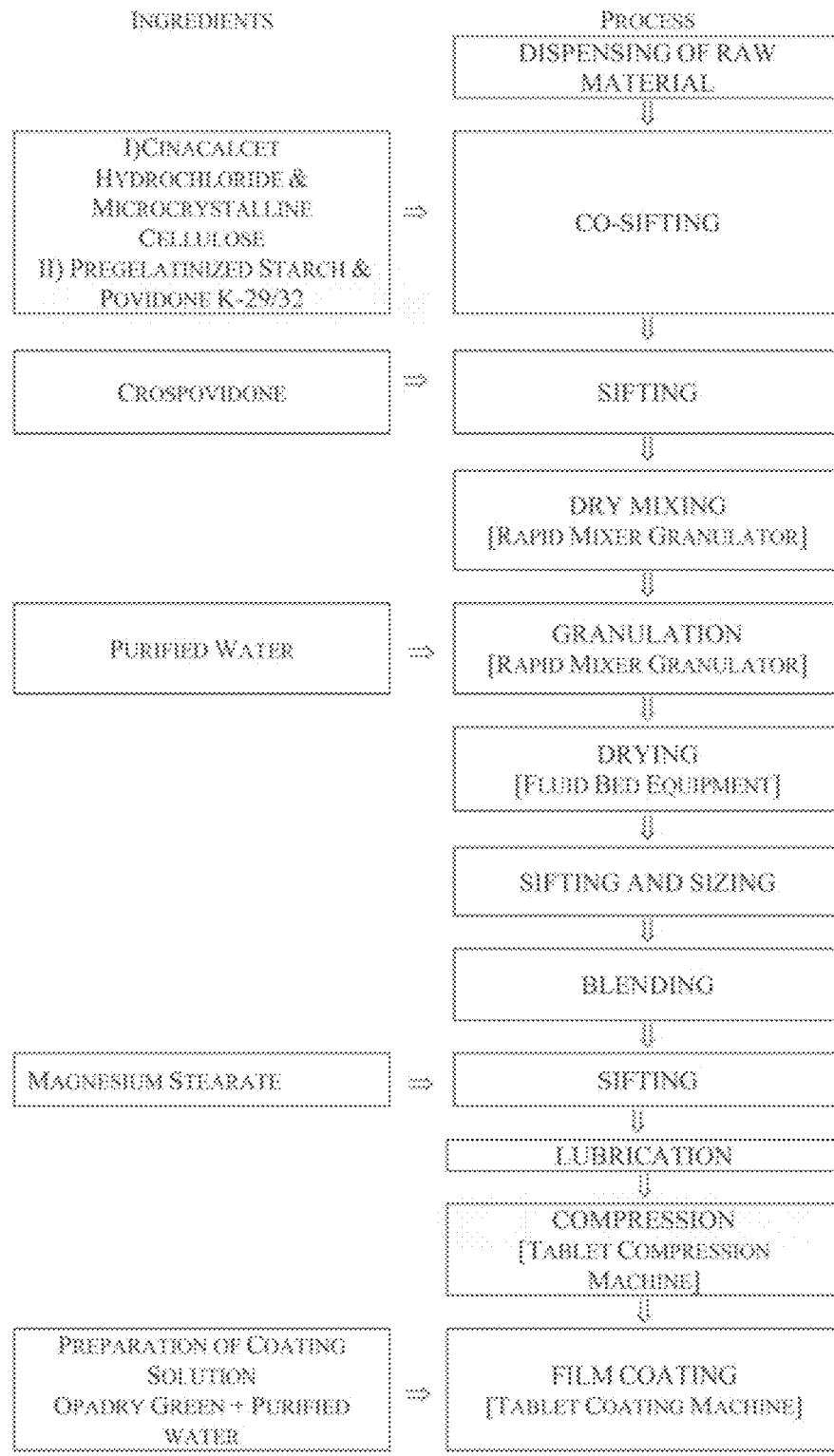
FIG. 1 is a flow chart for process for manufacturing of cinacalcet tablets 30 mg, 60 mg and 90 mg.
Figure 1:
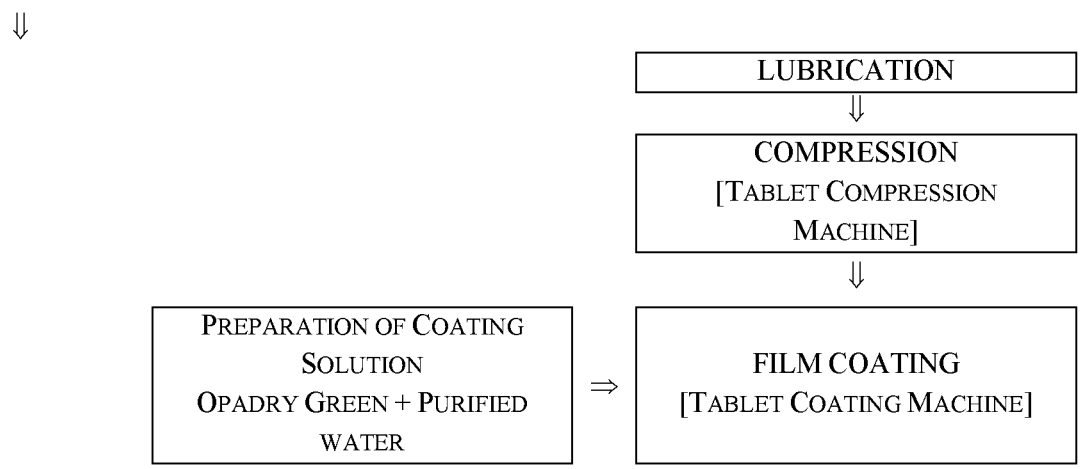
Figure 2:
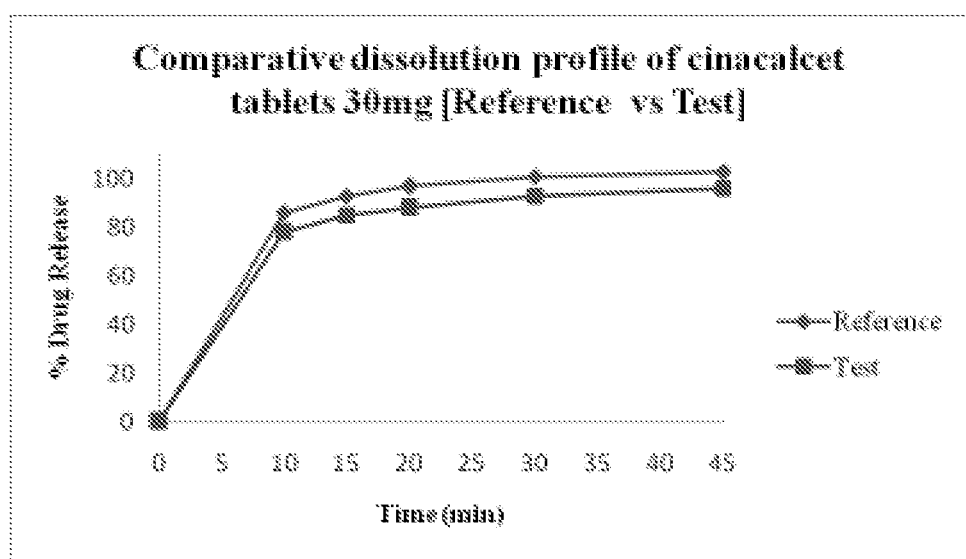
FIG. 2 is a graph depicting a comparative dissolution profile of Reference—[Sensipar®] cinacalcet tablets 30 mg and Test—cinacalcet tablets 30 mg as per one of the embodiment of the present invention.
Figure 3:
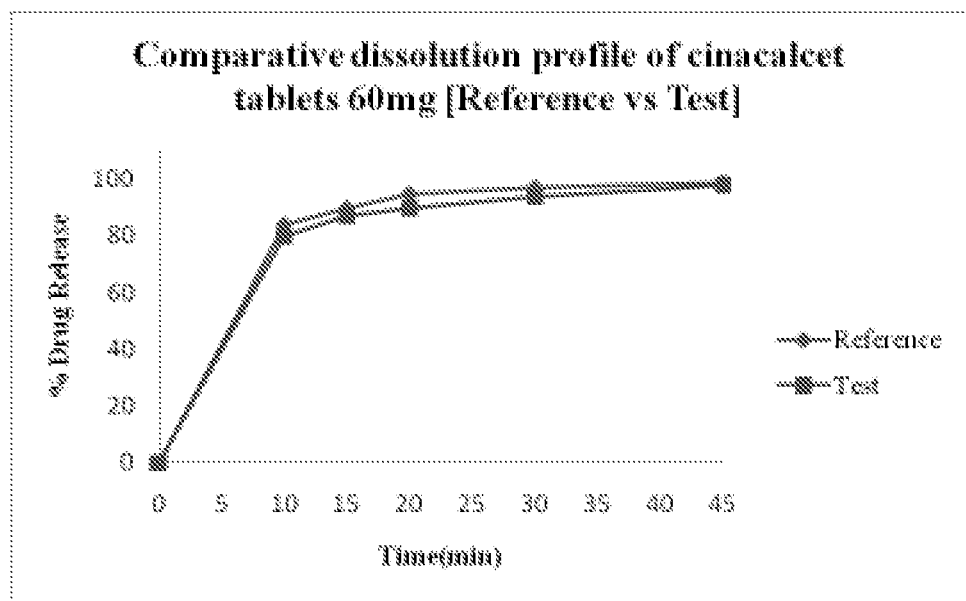
FIG. 3 is graph depicting a comparative dissolution profile of Reference—[Sensipar®] cinacalcet tablets 60 mg and Test—cinacalcet tablets 60 mg as per one of the embodiment of the present invention.
Figure 4:
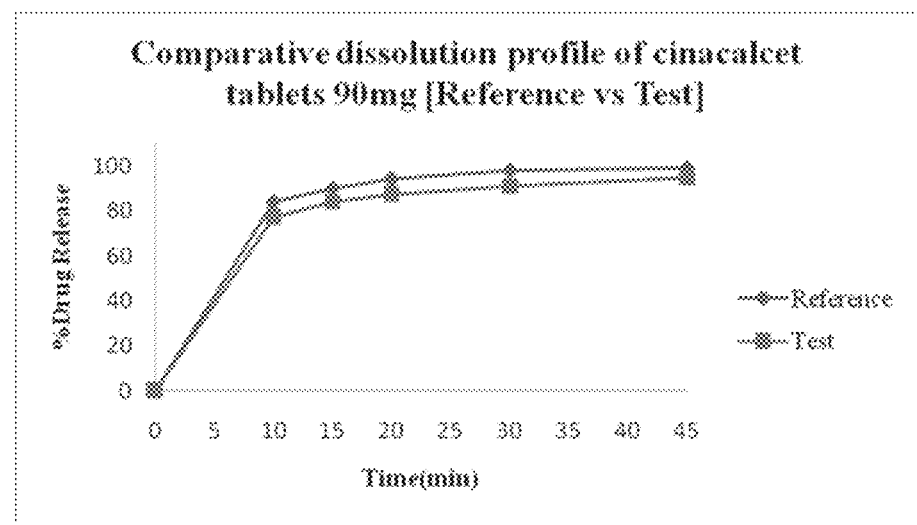
FIG. 4 is a graph depicting a comparative dissolution profile of Reference—[Sensipar®]cinacalcet tablets 90 mg and Test—cinacalcet tablets 90 mg as per one of the embodiment of the present invention.

Various objects, features, aspects and advantages of the inventive subject matter will become more apparent from the following detailed description of preferred embodiments.

DETAILED DESCRIPTION OF THE INVENTION

The invention will now be described in detail in connection with certain preferred and optional embodiments, so that various aspects thereof may be more fully understood and appreciated.

The term "Cinacalcet" refers to cinacalcet in the form of any pharmaceutically acceptable salts or derivatives thereof, including polymorphs, hydrates, solvates or amorphous forms, preferably cinacalcet is used in cinacalcet hydrochloride salt form, more preferably cinacalcet is used in micronized cinacalcet hydrochloride salt form in the formulation of the present invention.

The term "composition" or 'pharmaceutical composition" or "dosage form" as used herein interchangeably includes solid dosage forms such as but not limited to granules, pellets, micro-pellets, spheres, cores, coated cores, pills, compressed tablets, mini tablets, layered tablets, beads, particles, capsules and the like, meant for oral administration.

The term "pharmaceutically acceptable" as used herein means that which is useful in preparing a pharmaceutical composition that is generally safe and non-toxic.

The term "excipient" means a pharmacologically inactive compound such as a diluent, a disintegrant, a lubricant, a glidant, a binder comprised in a pharmaceutical product. The excipients that are useful in preparing a pharmaceutical composition are generally safe, non-toxic and are acceptable for human use. Reference to an excipient includes both one and more than one such excipients.

The term "tablet" is intended to encompass compressed pharmaceutical dosage forms of all shape and size, whether coated or uncoated.

The term "binder" as used herein means a substance that helps bind the active ingredient and other excipients together in a tablet. Binder ensures that tablets and granules can be formed having desired and required mechanical strength.

The term "not free of binder" as used herein means that the amount of binder present in the composition of the present invention is more than 0%.

The term "stable and reproducible" as used herein means that the composition is stable when stored at stability conditions as per ICH stability guidelines as well as it is stable during shelf life of the product. The process described herein produces a stable and bioequivalent formulation repeatedly.

The term "bioequivalent" as used herein means that a formulation that has the same pharmacologic potency and bioavailability as another formulation containing same active agent at the same dose. Two products or formulations containing the same active ingredient are bioequivalent if their rates and extents of absorption i.e., bioavailability are the same.

The term "micronization" means the production of particles having particle size distribution D90 equal to or less than 20 µm, D50 equal to or less than 10 µm, and D10 equal to or less than 5 µm.

The term "reference" as used herein means the drug identified by the FDA as the drug product upon which an applicant relies in seeking approval of its Abbreviated New Drug Application (ANDA).

The term "ASTM" as used herein means American Society for Testing and Materials.

The term "RH" as used herein means Relative humidity.

The term "LOD" as used herein means Loss on drying.

The term 'similarity factor' or 'f2' as used herein refers to one way of comparing dissolution profiles of two different products. This model-independent mathematical approach compares the dissolution profile of the two products: test and reference or two strengths. Tests are recommended to be performed under the same test conditions. The dissolution time points for both the profiles should be the same. An f2 value of 50 or greater (50-100) ensures sameness or equivalence of two curves, and thus performance of the two products, in-vitro.

The present invention in a preferred embodiment provides a pharmaceutical composition comprising cinacalcet or pharmaceutically acceptable salts thereof and one or more binders in an amount of 0.9% w/w or less, relative to the total weight of the composition, wherein the composition is not free of binder. Inventors of the present invention surprisingly found that a composition comprising cinacalcet-hydrochloride and one or more binders in an amount of less than 0.9% w/w of total weight of the composition results into the stable, reproducible and bioequivalent product.

In one of the preferred embodiment, the pharmaceutical composition comprises cinacalcet hydrochloride as a preferred pharmaceutically acceptable salt of cinacalcet.

In a preferred embodiment, the pharmaceutical composition comprises micronized cinacalcet hydrochloride as a preferred pharmaceutically acceptable salt of cinacalcet.

In another preferred embodiment, the pharmaceutical composition of the present invention comprises cinacalcet hydrochloride crystal form I.

In an embodiment, micronized cinacalcet hydrochloride in accordance with the present invention is usually obtained by milling.

In an embodiment, the milling is performed by using milling apparatus such as but not limited to ball mill, jet mill, pin mill, classifier mill, cross beater mill, disk mill, mortar grinder and rotor mill or any combination thereof.

In a preferred embodiment, the present invention relates to a tablet composition comprising a therapeutically effective dose of cinacalcet hydrochloride having particle size distribution D90 equal to or less than 20 µm, preferably $D_{90}$ ranging from about 12 µm-20 µm, D50 equal to or less than 10 µm, preferably $D_{50}$ ranging from about 5-10 µm and D10 equal to or less than 5 preferably $D_{10}$ ranging from about 2 µm-5 µm.

In an embodiment, the particle size of cinacalcet hydrochloride can be measured by techniques such as Malvern Mastersizer and a like.

In an embodiment, the present invention provides an oral dosage forms comprising cinacalcet hydrochloride and at least one pharmaceutically acceptable excipient(s).

In an embodiment, the present invention can be formulated in the form of solid dosage forms selected from but not limited to granules, pellets, micro-pellets, spheres, cores, coated cores, pills, compressed tablets, mini tablets, layered tablets, beads, particles, capsules and the like.

In a preferred embodiment, the present invention can be formulated into immediate release tablets.

In an embodiment, the present invention provides the pharmaceutical composition comprising cinacalcet or pharmaceutically acceptable salts thereof and one or more binders in an amount of 0.9% w/w or less, relative to the total weight of the composition, wherein the composition is not free of binder.

In an embodiment, the present invention provides the pharmaceutical composition comprising cinacalcet or pharmaceutically acceptable salts thereof and one or more binders in an amount of 0.9% w/w or less, preferably about 0.7% w/w or less, more preferably about 0.4% w/w or less, relative to the total weight of the composition.

In an embodiment, the present invention provides the pharmaceutical composition comprising cinacalcet or pharmaceutically acceptable salts thereof and one binder in an amount of 0.9% w/w or less, relative to the total weight of the composition, wherein the composition is not free of binder.

In a preferred embodiment, the present invention provides the pharmaceutical composition comprising cinacalcet or pharmaceutically acceptable salts thereof and povidone in an amount of 0.9% w/w or less, preferably about 0.7% w/w or less, more preferably about 0.4% w/w or less, relative to the total weight of the composition.

In an embodiment, the present invention provides the pharmaceutical composition comprising cinacalcet or pharmaceutically acceptable salts thereof and multiple binders such that total weight of the binder or concentration of binder is less than 0.9% w/w or less, preferably about 0.7% w/w or less relative to the total weight of the composition.

In another embodiment the present invention provides the pharmaceutical composition comprising cinacalcet or pharmaceutically acceptable salts thereof and povidone present in an amount of 0.9% w/w or less, preferably about 0.7% w/w or less, more preferably about 0.4% w/w or less, relative to the total weight of the composition and pregelatinized starch in an amount of 0.9% w/w or less, preferably about 0.7% w/w or less, more preferably about 0.4% w/w or less, relative to the total weight of the composition, such that the total amount of binder does not exceed 0.9% w/w relative to the total weight of the composition.

In an embodiment, the oral dosage form further comprises one or more of the following excipients such as but not limited to binders, disintegrants, glidants, lubricants, diluents, sweeteners, thickening agents, preservatives, flavoring agents, plasticizers and coloring agent or any combinations thereof.

Diluents or fillers include but are not limited to microcrystalline cellulose, microfine cellulose, powdered cellulose, lactose, dibasic calcium phosphate, tribasic calcium phosphate, starch, pregelatinized starch, calcium carbonate, calcium sulfate, magnesium carbonate, magnesium oxide, dextrates, dextrin, dextrose, kaolin, maltodextrin, mannitol, sucrose, methyl dextrin and sorbitol or any combination thereof.

In a preferred embodiment of the present invention diluents used is microcrystalline cellulose, pregelatinized starch or any combination thereof.

The composition of the present invention preferably comprises from about 50% to about 90% of one or more diluents by weight based on the total weight of the composition.

Binders include but are not limited to, polyvinylpyrrolidone (povidone, PVP); polyethylene glycol (PEG); cross-linked polyvinylpyrrolidone; cellulose derivatives including hydroxymethyl cellulose, hydroxypropylcellulose, carboxymethylcellulose sodium, ethyl cellulose, hydroxyethylcellulose, and hydroxypropylmethylcellulose; sucrose; alginic acid or sodium alginate; carbomer; cottonseed oil; dextrin; dextrose; guar gum; hydrogenated vegetable oil type I; magnesium aluminium silicate; maltodextrin; maltose; polydextrose; polyethylene oxide stearic acid and zein or combination thereof.

One or more binders are preferably used in an amount of from about 0.2% to about 0.7% by weight based on the total weight of the composition.

A preferred binder is povidone or various commercially available grades thereof.

Disintegrants include, but are not limited to carboxymethylcellulose calcium, carboxymethylcellulose sodium, croscarmellose sodium, crospovidone, polacrilin potassium, sodium alginate and sodium starch glycolate or any combination thereof.

Disintegrants are preferably used in an amount of from about 0.5% to about 6.0% by weight based on the total weight of the composition.

A preferred disintegrant is crospovidone.

Lubricants include, but are not limited to magnesium stearate, aluminium stearate, sucrose stearate, stearic acid, talc, fumaric acid, palmitic acid, sodium stearyl fumarate, glyceryl monostearate, carnauba wax, hydrogenated vegetable oils, mineral oil, polyethylene glycols or combination thereof.

Lubricants are preferably used in an amount of from about 0.1% to about 2.0% by weight based on the total weight of the composition.

In an embodiment of the present invention the pharmaceutically acceptable excipients to be used in accordance with the present invention can be used only intragranularly, only extragranularly or both.

In one of the preferred embodiment, the tablet of the present application optionally be coated with a film coat, which provides an aesthetic appeal. Film coat also provides moisture protection, taste masking etc.

Film coating material suitable for present application include but not limited to polyvinyl alcohol, hydroxypropyl methylcellulose, carboxymethyl cellulose and like. Preferably the coating is carried out using coating agents for example Opadry®. Preferred Opadry® isOpadry II Green which contains hypromellose, titanium dioxide, lactose monohydrate, triacetin, yellow iron oxide, FD&C Blue #2/indigo carmine aluminum lake.

In yet another embodiment, the present invention provides a stable cinacalcet hydrochloride composition when subjected to 40±2° C./75±5% RH accelerated stability condition.

In an embodiment of the invention, the pharmaceutical compositions as described herein may be prepared by processes known to a person having ordinary skill in the art of pharmaceutical technology such as direct compression, wet granulation, dry granulation or melt granulation.

In one embodiment the present invention provides a process for preparation of a pharmaceutical composition comprising cinacalcet or pharmaceutically acceptable salts thereof and one or more pharmaceutically acceptable excipients, wherein the process comprises steps of:
  a) mixing cinacalcet or pharmaceutically acceptable salts thereof with one or more pharmaceutically acceptable excipients;
  b) granulating the mixture obtained in step a);
  c) drying the granules obtained in step b) followed by blending, lubrication and compression; and
  d) optionally coating the dosage form obtained in step c).

In one embodiment the present invention provides a process of preparing a pharmaceutical composition comprising cinacalcet or pharmaceutically acceptable salts thereof according to any one of the preceding claims, comprising the steps of:

a) sifting cinacalcet or pharmaceutically acceptable salts thereof, binder(s) and pharmaceutical acceptable excipient(s);
b) mixing the sifted ingredients of step a) into rapid mixer grinder (RMG);
c) granulating the dry mixed material obtained in step b) with purified water;
d) drying the granules obtained in step c) in fluid bed dryer (FBD) until the loss on drying (LOD) ranging from 2.0-4.0% w/w is achieved;
e) sifting the dried granules of step d) through sieve of mesh 30 #ASTM and mixing;
f) lubricating the granules and compressing into the tablets; and optionally coating the tablets.

In a preferred embodiment the present invention provides a process for preparation of a pharmaceutical composition comprising cinacalcet or pharmaceutically acceptable salt thereof by wet granulation process, wherein the process comprises the steps of:

a) sifting cinacalcet hydrochloride, one or more diluent, one or more binders through #40 sieve;
b) sifting a disintegrant through #30 sieve;
c) transferring the sifted ingredients of step a) and b) in rapid mixer granulator (RMG) and mixing for 10 minutes to prepare dry mix;
d) granulating the dry mix of step c) with purified water;
e) drying the granules obtained in step d) in fluid bed dryer (FBD) to achieve the required loss on drying (LOD) ranging from 2.0-4.0% w/w is achieved;
f) sifting the dried granules of step e) through #30 ASTM sieve using vibrosifter and mixing from 10 minutes;
g) lubricating the sifted granules of step f) to obtain lubricated blend;
h) compressing the lubricated blend of step g) to obtain tablets; and
i) optionally coating the compressed tablets of step h).

In an embodiment, the pharmaceutical composition of the present invention comprises about 30 mg to about 90 mg cinacalcet as a free base.

In one of the preferred embodiment the pharmaceutical composition comprises about 33 mg to about 99 mg of cinacalcet hydrochloride equivalent to the free base.

In yet another embodiment, the composition of the present invention is useful for the treatment of at least one disease selected from hyperparathyroidism, parathyroid carcinoma, hypercalcemia in a patient in need thereof.

EXAMPLES

The present invention will be described in more detail by way of the following illustrative examples. It should be understood, however, that the present invention or the examples provided herein below are not limited to the specific details, components, conditions described in these examples, and the scope of the present invention is not limited thereto.

Example 1

Composition comprising 30 mg, 60 mg, and 90 mg of Cinacalcet Hydrochloride and preparation of tablet dosage form there from:

TABLE 1

Composition comprising 30 mg, 60 mg, and 90 mg of Cinacalcet Hydrochloride

| Sr. No. | Ingredients | Quantity (mg/Tab) | | |
| --- | --- | --- | --- | --- |
| | | 30 mg | 60 mg | 90 mg |
| Core Tablet | | | | |
| Dry Mix | | | | |
| 1 | Cinacalcet Hydrochloride | 33.06* | 66.12** | 99.18*** |
| 2 | Pregelatinized Starch | 0.65 | 1.3 | 1.95 |
| 3 | Microcrystalline Cellulose | 135.66 | 271.32 | 406.98 |
| 4 | Crospovidone | 9.08 | 18.16 | 27.24 |
| 5 | Povidone K29/30 | 0.65 | 1.3 | 1.95 |
| Granulating Agent | | | | |
| 6 | Purified water | q.s | q.s | q.s |
| Lubrication | | | | |
| 7 | Magnesium Stearate | 0.9 | 1.8 | 2.7 |
| | Total theoretical weight of core tablet (mg) | 180 | 360 | 540 |
| Film Coating | | | | |
| 8 | Opadry Green | 5.4 | 10.8 | 16.2 |
| 9 | Purified water | q.s. | q.s | q.s |
| | Total theoretical weight of coated tablet (mg) | 185.4 | 370.8 | 556.2 |

*33.06 mg of Cinacalcet Hydrochloride is equivalent to 30 mg Cinacalcet;
**66.12 mg of Cinacalcet Hydrochloride is equivalent to 60 mg Cinacalcet and
***99.18 mg of Cinacalcet Hydrochloride is equivalent to 90 mg Cinacalcet Manufacturing Procedure:

a) All the ingredients as per unit formula were dispensed maintaining the temperature less than 25° C. and RH less than 50%.
b) Cinacalcet Hydrochloride and Microcrystalline Cellulose were co sifted through mesh 40 #ASTM.
c) Pregelatinized Starch and Povidone K-29/32 were co sifted through 40 #ASTM.
d) Crospovidone was sifted through 30 #ASTM.
e) Sifted ingredients of step b), c) and d) were transferred into RMG & mixed for 10 minutes.
f) The contents of step e) were granulated with purified water.
g) The granules of step f) were dried in FBD till the desired LOD (2.0-4.0% w/w) was achieved.
h) Dried granules were passed through mesh 30 #ASTM.
i) The sifted granules were transferred into blender and mixed for 10 min at 16 rpm.
j) The content of step i) was lubricated using sifted Magnesium Stearate (mesh 40 #ASTM) for 3 min at 16 rpm.
k) The lubricated blend was compressed into tablets for all strengths.
l) The punch dimensions for 30 mg strength, 9.70×6.10 mm oval shape, standard concave.

m) The punch dimensions for 60 mg strength, 12.40×7.80 mm oval shape, standard concave.
n) The punch dimensions for 90 mg strength, 14.20×8.90 mm oval shape, standard concave.
o) Film coating solution: Opadry Green was dispersed in purified water under continuous stirring for 45 min.
p) The compressed tablets were coated using coating solution.

Example 2

Composition comprising 30 mg, 60 mg, and 90 mg of Cinacalcet Hydrochloride and preparation of tablet dosage form there from:

TABLE 2

Composition comprising 30 mg, 60 mg, and 90 mg of Cinacalcet Hydrochloride

| | Ingredients | Quantity (mg/Tab) | | | % |
|---|---|---|---|---|---|
| | | 30 mg | 60 mg | 90 mg | |
| A] Granulation | | | | | |
| 1 | Cinacalcet HCl | 33.06 | 66.12 | 99.18 | 17.83 |
| 2 | Pregelatinized Starch 1500 | 61.4 | 122.8 | 184.2 | 33.12 |
| 3 | Microcrystalline Cellulose | 74.83 | 149.66 | 224.48 | 40.36 |
| 4 | Crospovidone | 9.08 | 18.16 | 27.24 | 4.9 |
| 5 | Povidone | 0.73 | 1.46 | 2.20 | 0.4 |
| B] Binder | | | | | |
| 6 | Purified Water | q.s. | q.s. | q.s. | q.s. |
| Lubrication | | | | | |
| 7 | Sodium Stearyl Fumarate | 0.9 | 1.8 | 2.7 | 0.49 |
| C] Avg. wt of core Tablets | | 180 | 360 | 540 | 97.09 |
| Coating | | | | | |
| 8 | Opadry II Green | 5.40 | 10.80 | 16.20 | 2.91 |
| Avg. wt of coated Tablets | | 185.4 | 370.8 | 556.2 | 100 |

Manufacturing procedure:
a) Cinacalcet hydrochloride, microcrystalline cellulose, pregelatinized Starch 1500, crospovidone and povidone were sifted through #40 sieve.
b) the above sifted ingredients were transferred in rapid mixer granulator (RMG) and mixed.
c) Granulation was carried out with purified water.
d) The wet mass was dried in Fluid bed dryer to achieve the LOD of NMT 2% w/w.
e) The dried granules of step d) were sifted through #30 sieve.
f) The sifted granules were lubricated by using sodium stearyl fumarate.
g) The lubricated blend was compressed using specified punch.
h) The compressed tablets were coated using Opadry II Green coating solution.

Example 3

Micronization of Cinacalcet Hydrochloride:
Micronization of cinacalcet hydrochloride was carried out by Jet Milling. Particle size of micronized cinacalcet hydrochloride was measured with Malvern Mastersizer. Micronized cinacalcet hydrochloride was found to have particle size distribution D90 equal to or less than 20 μm, D50 equal to or less than 10 μm, and D10 equal to or less than 5 μm as can be seen below Table 1 showing the particle size distribution of different batches of the micronized cinacalcet hydrochloride.

TABLE 3

Particle size distribution of different batches of the micronized cinacalcet hydrochloride

| Sr. | Batch Number | $D_{90}$ | $D_{50}$ | $D_{10}$ |
|---|---|---|---|---|
| 1. | Batch No 60002 | 18.8 μm | 9.58 μm | 4.06 μm |
| 2. | Batch No 70001 | 13.4 μm | 6.55 μm | 2.66 μm |
| 3. | Batch No 70002 | 15.4 μm | 6.81 μm | 2.35 μm |

Comparison of in-vitro dissolution profile:
The tablets of cinacalcet hydrochloride prepared as per the composition of Example 1 were subjected to dissolution studies.
Table 4: Provides comparative dissolution profiles of Sensipar® 30 mg, 60 mg & 90 mg (RLD) herein referred as 'reference' versus cinacalcet tablets 30 mg, 60 mg & 90 mg as per composition of Example 1, herein referred to as 'test' in 900 ml 0.05 N HCl, apparatus USP type II (Paddle), 75 RPM, at 37±0.5° C.

TABLE 4

Dissolution data of cinacalcet tablets 30 mg, 60 mg and 90 mg [Reference vs Test]

| Method | Time points (minutes) | Cinacalcet tablets 30 mg | | Cinacalcet tablets 60 mg | | Cinacalcet tablets 90 mg | |
|---|---|---|---|---|---|---|---|
| | | Reference | Test | Reference | Test | Reference | Test |
| Paddle, | 10 | 86 | 78 | 84 | 80 | 84 | 77 |
| 75 rpm, | 15 | 93 | 85 | 90 | 87 | 90 | 84 |
| 900 mL, | 20 | 97 | 88 | 95 | 90 | 94 | 87 |
| 0.05N | 30 | 101 | 93 | 97 | 94 | 98 | 91 |
| HCl | 45 | 103 | 96 | 99 | 98 | 99 | 95 |
| F2 value | | 54.61 | | 72.15 | | 59.73 | |

Stability Data:

Table 5, Table 6 and Table 7: Provides initial 1M, 2M, 3M & 6M accelerated stability data of cinacalcet tablets 30 mg, 60 mg and 90 mg as per composition of example 1 packed in HDPE container.

TABLE 5

Accelerated stability data of cinacalcet tablets 30 mg [Test product-HDPE pack]

| Sr. | Parameters | Limits | Initial | 40° C./75% RH | | | |
|---|---|---|---|---|---|---|---|
| | | | | 1 M | 2 M | 3 M | 6 M |
| 1. | Description | Light green coloured, film coated, oval shaped tablets debossed with '257' on one side and 'U' on other side. | Light green coloured, film coated, oval shaped tablets debossed with '257' on one side and 'U' on other side. | Complies | Complies | Complies | Complies |
| 2. | % Dissolution | NLT 75% (Q) of the labelled amount of Cinacalcet is dissolved in 45 min. | 96 | 94 | 98 | 90 | 90 |
| 3. | | Related substances (%) | | | | | |
| a. | Any individual unspecified impurity | NMT 0.20% | 0.06 | 0.06 | 0.06 | 0.06 | 0.06 |
| b. | Total Impurities (Sum of all the individual impurities ≥ 0.05%[1)] | NMT 0.60% | 0.06 | 0.06 | 0.06 | 0.06 | 0.06 |
| 4. | Assay | Between 90% to 110% of label claim | 99.9 | 98.7 | 99.7 | 101.3 | 98.0 |

TABLE 6

Accelerated stability data of cinacalcet tablets 60 mg [Test product-HDPE pack]

| Sr. | Parameters | Limits | Initial | 40° C./75% RH | | | |
|---|---|---|---|---|---|---|---|
| | | | | 1 M | 2 M | 3 M | 6 M |
| 1. | Description | Light green coloured, film coated, oval shaped tablets debossed with '258' on one side and 'U' on other side. | Light green coloured, film coated, oval shaped tablets debossed with '258' on one side and 'U' on other side. | Complies | Complies | Complies | Complies |
| 2. | % Dissolution | NLT 75% (Q) of the labelled amount of Cinacalcet is dissolved in 45 min. | 98 | 94 | 91 | 91 | 92 |
| 3. | | Related substances (%) | | | | | |
| a. | Any individual unspecified impurity | NMT 0.20% | 0.06 | 0.06 | 0.07 | 0.06 | 0.06 |
| b. | Total Impurities (Sum of all the individual impurities ≥ 0.05%[1)] | NMT 0.60% | 0.06 | 0.06 | 0.07 | 0.06 | 0.06 |
| 4. | Assay | Between 90% to 110% of label claim | 101.2 | 99.5 | 101.0 | 99.7 | 99.7 |

TABLE 7

Accelerated stability data of cinacalcet tablets 90 mg [Test product-HDPE pack]

| Sr. | Parameters | Limits | Initial | 40° C./75% RH | | | |
|---|---|---|---|---|---|---|---|
| | | | | 1 M | 2 M | 3 M | 6 M |
| 1. | Description | Light green coloured, film coated, oval shaped tablets debossed with '259' on one side and 'U' on other side. | Light green coloured, film coated, oval shaped tablets debossed with '259' on one side and 'U' on other side. | Complies | Complies | Complies | Complies |
| 2. | % Dissolution | NLT 75% (Q) of the labelled amount of Cinacalcet is dissolved in 45 min. | 95 | 97 | 90 | 92 | 94 |
| 3. | Related substances (%) | | | | | | |
| a. | Any individual unspecified impurity | NMT 0.20% | 0.06 | 0.06 | 0.07 | 0.06 | 0.06 |
| b. | Total Impurities (Sum of all the individual impurities ≥ 0.05%[1]) | NMT 0.60% | 0.06 | 0.06 | 0.07 | 0.06 | 0.06 |
| 4. | Assay | Between 90% to 110% of label claim | 101.1 | 100.3 | 100.1 | 98.2 | 96.5 |

TABLE 8

Bioequivalence Summary Table of Cmax:

| Treatment | Ratio | 90% CI |
|---|---|---|
| Test product 90 mg REFERENCE Product 90 mg | 89.88 | (81.37, 99.28) |

TABLE 9

Bioequivalence Summary Table of AUC 0-t

| Treatment | Ratio | 90% CI |
|---|---|---|
| Test product 90 mg REFERENCE Product | 89.85 | (83.52, 96.67) |

TABLE 10

Bioequivalence Summary Table of AUC 0-inf

| Treatment | Ratio | 90% CI |
|---|---|---|
| Test product 90 mg REFERENCE Product | 90.04 | (83.89, 96.63) |

We claim:

1. A pharmaceutical composition, comprising:
   (a) cinacalcet or a pharmaceutically acceptable salt thereof; wherein particle size distribution of cinacalcet or a pharmaceutically acceptable salt thereof is $D_{90}$ in the range of 13.4 μm to 18.8 μm, $D_{50}$ in the range of 6.55 μm to 9.58 μm, and $D_{10}$ in the range of 2.35 μm to 4.06 μm:
   (b) a binder consisting of (i) pregelatinized starch and (ii) povidone, in an amount of about 0.9% w/w or less, relative to the total weight of the composition; and
   (c) optionally a pharmaceutically acceptable excipient.

2. The pharmaceutical composition according to claim 1, wherein the pharmaceutical composition is selected from the group consisting of granules, pellets, micro-pellets, spheres, cores, coated cores, pills, compressed tablets, mini tablets, layered tablets, beads, particles and capsules.

3. The pharmaceutical composition according to claim 1, wherein the pharmaceutical composition is in the form of compressed tablets.

4. The pharmaceutical composition according to claim 1, wherein the pharmaceutically acceptable excipient is at least one selected from the group consisting of a diluent, a disintegrant, a lubricant, and a glidant.

5. The pharmaceutical composition according to claim 1, wherein the povidone as a binder is present in an amount from about 0.35% w/w to less than about 0.9% w/w, relative to total weight of the composition.

6. The pharmaceutical composition according to claim 1, wherein the pregelatinized starch as a binder is present in an amount from about 0.35% w/w to less than about 0.9% w/w, relative to total weight of the composition.

7. The pharmaceutical composition according to claim 4, wherein the excipient is a diluent, wherein the diluent is microcrystalline cellulose, microfine cellulose, powdered cellulose, lactose, dibasic calcium phosphate, tribasic calcium phosphate, starch, pregelatinized starch, calcium carbonate, calcium sulfate, magnesium carbonate, magnesium oxide, dextrates, dextrin, dextrose, kaolin, maltodextrin, mannitol, sucrose, methyl dextrin, sorbitol or a combination thereof.

8. The pharmaceutical composition according to claim 4, wherein the excipient is a disintegrant, wherein the disintegrant is carboxymethylcellulose, calcium, carboxymethylcellulose sodium, croscarmellose sodium, crospovidone, polacrilin potassium, sodium alginate, sodium starch glycolate or a combination thereof.

9. The pharmaceutical composition according to claim 2, wherein the excipient is a lubricant, wherein the lubricant is magnesium stearate, aluminium stearate, sucrose stearate, stearic acid, talc, fumaric acid, palmitic acid, sodium stearyl fumarate, glyceryl monostearate, carnauba wax, hydrogenated vegetable oils, mineral oil, polyethylene glycols or a combination thereof.

10. A process of preparing a pharmaceutical composition comprising cinacalcet or a pharmaceutically acceptable salt thereof according to claim 1, the process comprising:
   a) sifting cinacalcet or a pharmaceutically acceptable salt thereof, a binder, and a pharmaceutical acceptable excipient to obtain sifted ingredients;
   b) mixing the sifted ingredients of a) into a rapid mixer granulator (RMG) to obtain dry mixed material;
   c) granulating the dry mixed material obtained in b) with purified water to obtain granules;
   d) drying the granules obtained in c) in a fluid bed dryer (FBD) until a loss on drying (LOD) ranging from 2.0-4.0% w/w is achieved to obtain dried granules;
   e) sifting the dried granules of d) through sieve of mesh 30 #ASTM and mixing; and
   f) lubricating the granules and compressing into tablets, and optionally coating the tablets.

11. A process for treating hyperparathyroidism, parathyroid carcinoma, or hypercalcemia, comprising: administering the pharmaceutical composition according to claim 1 to a patient in need thereof.

12. The pharmaceutical composition according to claim 1, wherein the binder is present in an amount from about 0.35% to about 0.7% w/w of total weight of the composition.

\* \* \* \* \*